(12) United States Patent
Szatkowski

(10) Patent No.: US 10,859,550 B2
(45) Date of Patent: Dec. 8, 2020

(54) THERMAL SURFACE CASING VENT-STEAM CONDENSING GAS AND FLUID FLOW RATE-COLLECTION MANIFOLD

(71) Applicant: Bryan Szatkowski, Lloydminster (CA)

(72) Inventor: Bryan Szatkowski, Lloydminster (CA)

( * ) Notice: Subject to any disclaimer, the term of this patent is extended or adjusted under 35 U.S.C. 154(b) by 148 days.

(21) Appl. No.: 15/981,301

(22) Filed: May 16, 2018

(65) Prior Publication Data
US 2018/0372702 A1    Dec. 27, 2018

Related U.S. Application Data

(60) Provisional application No. 62/507,043, filed on May 16, 2017.

(51) Int. Cl.
| G01N 33/00 | (2006.01) |
| E21B 49/08 | (2006.01) |
| E21B 43/24 | (2006.01) |
| G01N 33/24 | (2006.01) |

(52) U.S. Cl.
CPC ....... *G01N 33/006* (2013.01); *E21B 43/2406* (2013.01); *E21B 49/086* (2013.01); *G01N 33/0044* (2013.01); *G01N 33/0047* (2013.01); *G01N 33/241* (2013.01); *E21B 49/0875* (2020.05)

(58) Field of Classification Search
CPC ............ G01N 33/006; G01N 33/0044; G01N 33/0047; G01N 33/241; E21B 49/086; E21B 43/2406; E21B 2049/085
See application file for complete search history.

(56) References Cited

U.S. PATENT DOCUMENTS

| 3,303,872 A | * | 2/1967 | Leonard, Jr. | F25B 1/053 165/62 |
| 4,251,220 A | * | 2/1981 | Larson | G01N 27/06 210/662 |
| 5,102,616 A | * | 4/1992 | Gardner | G21C 1/322 376/282 |
| 5,102,617 A | * | 4/1992 | Gluntz | G21C 9/004 376/283 |
| 5,139,083 A | * | 8/1992 | Larinoff | F28B 1/06 165/113 |
| 5,475,720 A | * | 12/1995 | Oldenhage | G21C 17/035 376/258 |
| 7,568,523 B2 | * | 8/2009 | Smith | B01D 17/044 166/267 |
| 2004/0148941 A1 | * | 8/2004 | Wylie | F01K 23/103 60/772 |
| 2005/0109032 A1 | * | 5/2005 | Harpster | F28B 1/02 60/685 |

(Continued)

*Primary Examiner* — Shogo Sasaki
(74) *Attorney, Agent, or Firm* — James A. Sheridan; Sheridan Law, LLC

(57) ABSTRACT

A novel gas and fluid measurement system is provided that can assess undesired gas or fluid leakage in surface casing vents at wellbores or facilities under thermal production enhancement. The system can remove water vapour (steam and/or liquid water) from the gas flow, measure flow rates and volumes of fluids and gases, contain representative fluid and gas samples for collection, and monitor and measure, in real-time, the sulphur gas content, physical water parameters and combustible gas content.

6 Claims, 8 Drawing Sheets

(56) References Cited

U.S. PATENT DOCUMENTS

2007/0114025 A1\* 5/2007 Smith .................. E21B 21/063
  166/267
2007/0144785 A1\* 6/2007 Smith .................... B01D 17/06
  175/66

\* cited by examiner

THERMAL SURFACE CASING VENT-STEAM CONDENSING GAS AND FLUID FLOW RATE-COLLECTION MANIFOLD

CROSS-REFERENCE TO RELATED APPLICATIONS

This application claims priority of U.S. provisional patent application Ser. No. 62/507,043 filed May 16, 2017, which is incorporated by reference into this application in its entirety.

TECHNICAL FIELD

The present disclosure is related to the oil and gas industry in the field of production and environmental engineering for detection, measurement, repair and monitoring of gases or fluids released from the surface casing vent ("SCV") of producing, injection or monitoring well bores at cold or thermal enhanced bitumen production facilities.

BACKGROUND

Gases or fluids flow from a surface casing vent or surface casing vent flow ("SCVF"), is considered to be an environmental, health and safety and fire hazard. All regulatory jurisdictions in Canada have procedures and policies regarding the testing and monitoring of SCVs for gas and fluid flow although these can vary greatly. As well these jurisdictions have different and varying rules and regulations (timing, procedures, etc.) regarding the remediation and repair of these flows however all jurisdictions agree that SCVF is undesirable.

Accurate measurements of gas and fluid release rates and volumes and collection and containment of representative samples for geochemical measurements (chemical and isotopic compositions) in thermally enhanced production facilities can be a challenging task. In addition, obtaining representative gas and fluid samples for geochemical measurements (chemical and isotopic compositions) to classify, characterize and determine the geological origins of venting gases or fluids is also complicated as a result of variable site conditions, high water contents, high well head temperatures and the presence of sulphur gases.

In western Canada, many oil and gas wells are leaking gas and fluids into the surface casing vent. Fugitive gases and fluids may migrate into shallower strata impacting shallow aquifers, soils and, ultimately, may be released to atmosphere. This undesired leakage, or migration, of natural gases from deep (thermogenic) sources poses significant operational, health and safety and environmental concerns. Gaseous hydrocarbons or fluids may enter a well bore at points of poor cement bonding with wall rock, in small, and possibly gas induced channels within the cement itself, or in micro-annuli at the contact between casing and cement. Where gas is detected in the vent between the production and surface casing, it is considered to be surface casing vent flow (SCVF). At wellbores undergoing thermally enhanced production, for example, steam-assisted gravity drainage ("SAGD") or cyclic steam stimulation ("CSS"), SCVF can be comprised of natural gases and fluids from formation, water vapour or water, hydrogen generated near the wellbore by cathodic reactions, methane and carbon dioxide from biogenic activity, heavier alkanes from the breakdown of hydrocarbon liquids, helium from natural deep mantle processes, oxygen, nitrogen and argon, trace amounts of volatile organics and atmospheric gases, and/or various contaminants from chemicals used in drilling, completion and production processes.

Correct classification, characterization and identification of the origin of gases or fluids is critical for determining appropriate remediation and repair procedures. Identifying the geological origins of light hydrocarbons, carbon dioxide, sulphur gases or waters in surface casing vents has proven to be a challenging task in thermally enhanced oil recovery projects. Elevated wellhead temperatures, water vapor, condensed steam or physical water and the presence of sulphur gases in surface casing vents complicates gas or fluid leakage assessments.

Previously attempts have been made to measure flow rates and collect gas/fluid samples directly from the SCV. This results in erroneous flow measurements (cannot differentiate natural gas flow from water vapour flow) and unrepresentative samples collected. This method has been determined to be insufficient in all regards.

As well other apparatus have been developed that use various condensing systems in an attempt to remove the water vapour/water from the gas flow. These systems suffer from incomplete separations of water vapour and natural gas flows and, therefore, erroneous flow measurements. These systems also typically use "open system" water/fluid collection vessels that will allow evaporation of the water rendering fluid flow measurements erroneous. In addition, evaporation processes change the chemical compositions of the samples (concentrating components) and cause fractionation (changing) of the stable hydrogen and oxygen isotope compositions of the water.

Many of the versions use substandard flow measurement devices that are not optimized for detecting and accurately determining the natural gas flow rates over the range that may be observed, and do not have the ability to monitor and measure in-situ in real time, the $H_2S$ (sulfur gas) content, fluid parameters (TDS, pH, EC) or combustible gas content (% lower explosive limit ("LEL"), or methane content).

There is, therefore, a requirement for an apparatus that can: a) separate the water/fluid from the gas flow; b) accurately measure flow rates and volumes of natural gas and fluids; c) allow containment and collection of representative natural gas and fluid samples; and d) measure real time in-situ natural gas and fluid physical parameters.

SUMMARY

In some embodiments, a novel gas and fluid measurement system, more accurately referred to as a thermal-surface casing vent flow-steam condensing gas fluid flow rate-collection manifold ("T-SCVF-SC-GFFC-M") system, can be provided to assess undesired gas or fluid leakage in thermally enhanced surface casing vents. This system can remove water vapour (steam and/or liquid water) from the gas flow, measure flow rates and volumes of fluids and gases, contain representative fluid and gas samples for collection, and monitor and measure in real time the $H_2S$ (sulphur gas) content, physical water parameters (total dissolved solids ("TDS"), pH, electrical conductivity ("EC")) and combustible gas content (% LEL, or methane content).

In some embodiments, the system can employ multiple heat exchangers and water knock-outs to remove fluids from the gas flow. Fluids can be contained in a zero headspace collection container that prevents evaporation allowing for accurate volume measurements and minimizing evaporation allowing for collection of representative fluid samples. Using an air pressure system, samples can be collected during the well test without exposing the sample to atmosphere or opening the system (maintains zero headspace) and minimizing evaporation.

In some embodiments, the gas can be contained in a plunger system for collection of representative samples or directed to a suite of in-situ real time analytical instruments. Back pressure to the system can be minimized, and sample collection can be conducted without disrupting or halting the well test allowing for continuous monitoring.

In some embodiments, the gas flow can be contained, and accurate flow rates across a large range of flows (~0.0003 m$^3$/day to >360 m$^3$/day) can be measured using mass flow meters and pressure displacement meters. In some embodiments, temperatures and pressures throughout the apparatus can be measured and data-logged for quality assurance ("QA") or quality control ("QC"). Minimal pressure can be maintained throughout the system so that flows can be accurately measured and monitored.

Currently, a system to accurately establish and measure rates and volumes of venting gases or fluids at resource wells and collection of representative of samples for geochemical measurements is not available to accommodate the various scenarios present at each well bore, which can include:

1) Elevated well head temperatures due to steam injection or hot oil production.
2) Presence of high temperature steam associated with potentially leaking gases or fluids from SCVs.
3) Variable venting gas rate and volumes.
4) Variable venting fluid rates and volumes.
5) The presence of condensed steam (physical water) and non-condensed steam.
6) Isotopic fractionation effects of gases during the assessment process.
7) Isotopic fractionation effects of waters during the assessment process.
8) Presence of associated sulphur gases (i.e. H$_2$S).

In some embodiments, a T-SCVF-SC-GFFC-M system can be provided to address the foregoing, and to accommodate the following situations and scenarios:

1) Elevated well head temperatures due to steam injection or hot oil production.
   a. Parts exposed to elevated temperatures at the wellhead are constructed of heat resistant materials.
2) Presence of high temperature steam associated with potentially leaking gases or fluids from SCVs.
   a. Parts exposed to high temperature steam are constructed of heat resistance materials.
3) Variable venting gas rate and volumes.
   a. Multiple mass flow meters are used for flow rates above 0.003 m$^3$/day.
   b. A pressure displacement ("PD") meter is used for very low flow rates (0.0003 m$^3$/day to 0.003 m$^3$/day).
4) Variable venting fluid rates and volumes.
   a. The apparatus employees a zero headspace fluid sample container system that is able to change volume with increasing sample volumes from very low volume to maximum container size with no/minimal headspace.
   b. The zero headspace fluid sample containers can be rapidly changed to accommodate high flow scenarios.
5) The presence of condensed steam (physical water) and non-condensed steam.
   a. A water knock-out is employed to remove liquids flowing from the SCV.
   b. A condensing unit lowers the temperature of the gas flow below 100° C. condensing the water vapour and then separating the fluid from the gas flow.
6) Isotopic fractionation effects of gases during the assessment process.
   a. Incomplete sample collection or leakage of gases is a significant fractionation process. This apparatus can be a closed system minimizing sample loss.
7) Isotopic fractionation effects of waters during the assessment process.
   a. Evaporation is a significant isotope fractionation event for liquids. A closed zero headspace fluid collection container can be used to minimize this effect.
8) Presence of associated sulphur gases (i.e. H$_2$S).
   a. All wetted parts can be Sulfinert® protected preventing sulfur gases from sticking to the inside of the apparatus allowing for accurate on site in-situ H$_2$S readings and representative sample collection for detailed speciated sulfur gas analysis.

In some embodiments, the system can also be expanded to include various analytical instruments to extend the real time in-situ monitoring, detection and measurement capabilities of the system. These additional instruments can include, but are not limited to:

1) Gas Chromatographs ("GC"), Gas Chromatograph Mass Spectrometers ("GC-MS") and other trace gas analyzers for in-situ, real time determination of the chemical composition of the gas flow (i.e. hydrocarbons, atmospheric gases, volatile organic compounds ("VOCs"), trace gases).
2) Off Axis Integrated Cavity Output Spectrograph ("OA-ICOS") or Cavity Ring Down Laser Spectrograph ("CRDS") for in-situ, real time stable isotope analysis and concentration of carbon in methane, stable isotope analysis of oxygen and carbon in and the concentration of carbon dioxide and the stable isotope analysis of oxygen and hydrogen in water.
3) Trace water component analysis in real time:
   a. Fourier Transform Infrared ("FTIR") spectrography,
   b. Ion chromatographs ("IC"),
   c. Liquid Chromatographs ("LC") and Liquid Chromatigraph Mass Spectrometers ("LC-MS"),
   d. Solid Phase Extraction ("SPE")

Broadly stated, in some embodiments, a gas and fluid measurement system can be provided, the system configured for collecting natural gas and fluids samples from a well casing vapour flux chamber that are isolated from the atmosphere, the system comprising: a primary water knock-out low heat exchanger configured for operatively coupling to the well casing vapour flux chamber and receiving a sample of natural gas and fluids therefrom, the primary heat exchanger configured for removing water from the sample at a low heat thereby producing a first processed sample; a primary pressure water bladder collection bag operatively coupled to the primary heat exchanger, the primary collection bag configured to receive the water removed by the primary heat exchanger; a secondary steam condenser high heat exchanger configured for operatively coupling to the primary heat exchanger and receiving the first processed sample, the secondary heat exchanger configured for removing further water from the sample at a high heat thereby producing a second processed sample; a secondary pressure water bladder collection bag operatively coupled to the secondary heat exchanger, the secondary collection bag configured to receive the water removed by the secondary heat exchanger; and a gas drier/conditioner configured for operatively coupling to the secondary heat exchanger and receiving the second processed sample, the gas drier/conditioner further configured to produce a primary gas sample.

Broadly stated, in some embodiments, the system can further comprise a gas collection manifold operatively coupled to the gas drier/conditioner, the manifold configured to isolate and collect gases without disrupting continuous monitoring, the manifold further configured to contain the gases with minimal isotope fractionation.

Broadly stated, in some embodiments, the system can further comprise at least one flow meter and a pressure displacement meter.

Broadly stated, in some embodiments, the system can further comprise at least one data-logger operatively coupled to the at least one flow meter and the pressure displacement meter, the at least one data-logger configured to measure, monitor and data-log gas flows, temperatures and pressures.

Broadly stated, in some embodiments, the system can further comprise at least one analytical instrument configured for real-time in-situ monitoring, detection and measurement of the second processed sample.

Broadly stated, in some embodiments, the at least one analytical instrument can comprise one or more of a group comprising of gas chromatographs, gas chromatograph spectrometers, trace gas analyzers, off-axis integrated cavity output spectrographs, cavity rind-down laser spectrographs, Fourier transform infrared spectrographs, ion chromatographs, liquid chromatographs, liquid chromatograph mass spectrometers and solid phase extraction devices.

DETAILED DESCRIPTION OF EMBODIMENTS

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
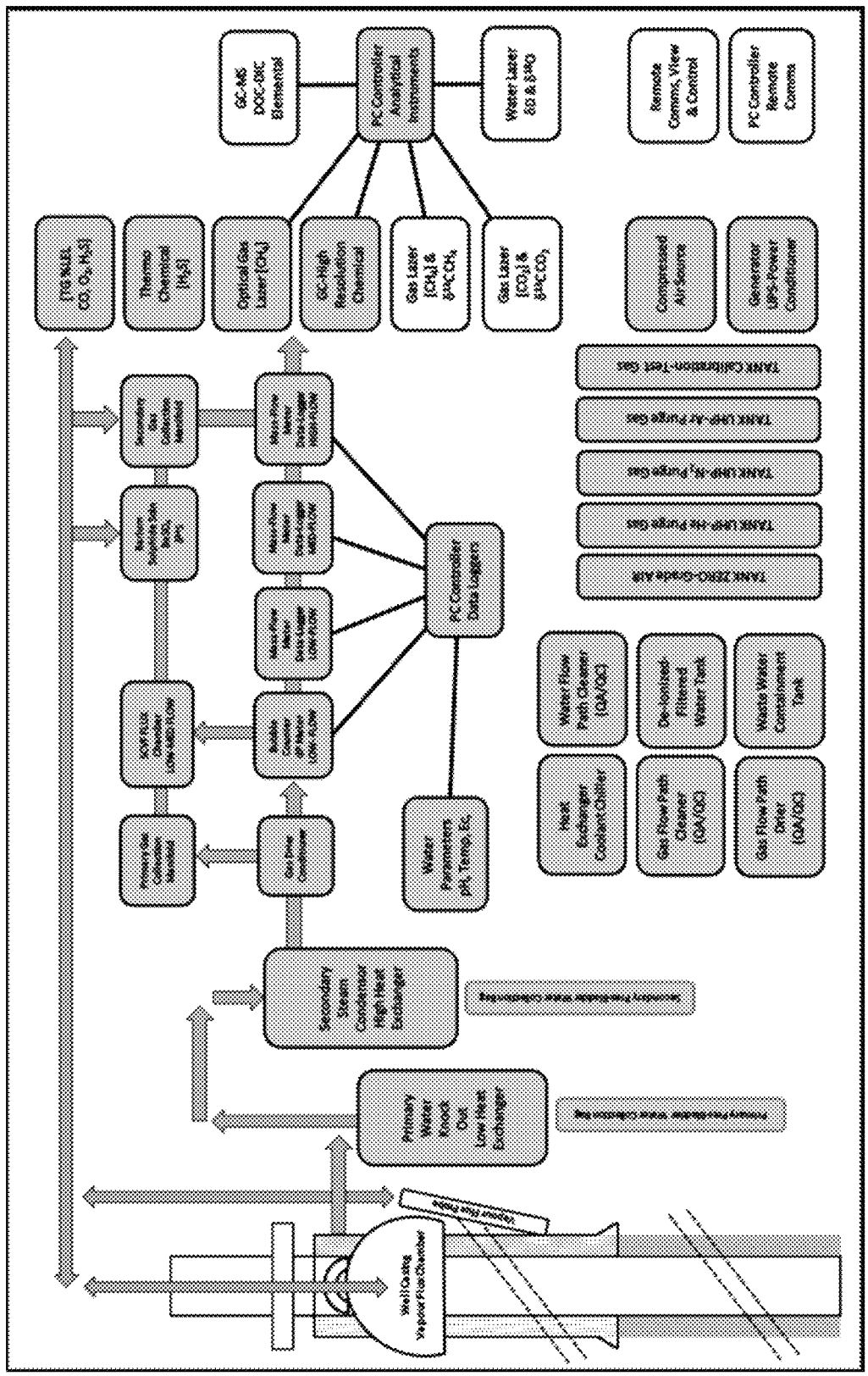
FIG. 1 is a block diagram depicting one embodiment of a novel gas and fluid measurement system.

Referring to FIG. 1, the system presented herein can comprise, in some embodiments, the following components:

Primary Water Knockout Low Heat Exchanger. In some embodiments, a primary heat exchanger can separate the water vapour from the gas flow. It can further decrease the temperature of the flow below maximum temperature thresholds of the rest of the system. Fluid flowing from the SCV or that condenses out of the flow in the primary heat exchanger can be directed to the Primary Pressure Bladder Collection Bag.

Primary Pressure Bladder Collection Bag. In some embodiments, a primary collection bag can collect fluid from the primary heat exchanger. In some embodiments, the system can use outside pressure to maintain zero headspace separating the fluid and gas, and to minimize evaporation processes that could alter the fluid composition. Pressure on the sample container bladder can be released as fluid is collected. When sampling is required, a valve can be opened and pressure can be exerted on the sample container bladder to force fluid out of the sample container bladder into a sample container for storage prior to analysis.

Secondary Steam Condenser High Heat Exchanger. In some embodiments, a secondary heat exchanger can remove water vapour from the gas flow, thereby allowing fluid to flow to the secondary pressure bladder water collection bag, and to allow gases to continue through the system.

Secondary Pressure Bladder Water Collection Bag. In some embodiments, a secondary collection bag can collect fluid from the secondary heat exchanger. In some embodiments, the system can use outside pressure to maintain zero headspace separating the fluid and gas, and to minimize evaporation processes that could alter the fluid composition. Pressure on the sample container bladder can be released as fluid is collected. When sampling is required, a valve can be opened and pressure can be exerted on the sample container bladder forcing fluid out of the sample container bladder into a sample container for storage prior to analysis.

Gas Dryer. In some embodiments, a final gas drying step can be employed to remove near 100% of the water moisture in the gas stream to prevent damage to measuring and analytical devices further upstream.

In some embodiments, gases can be collected by a primary gas collection manifold prior to continuing to the flow meters. The gas collection manifold can be used for gas analysis, and as a QA/QC method to ensure gases are not altered passing through the system.

If low flows are present, gases can bypass the primary gas collection manifold to a SCVF Flux Chamber. Here, gases are allowed to accumulate until a sufficient volume is present for representative sample collection.

If gases are not passed to the Primary Gas Collection Manifold or SCVF Flux Chamber, the gases can be directed to the mass flow meters and pressure displacement ("PD") meters, which can measure flow rates from 0.0003 m3/day to >360 m3/day. In some embodiments, personal computer ("PC") Controller Data-loggers can be used, wherein water parameters, flow rate, pressures, and temperatures can be data-logged and monitored at a central system.

In some embodiments, the gas flow can be directed either to various analytical instruments, or to the secondary gas collection manifold for sample collection. In some embodiments, a Secondary Gas Collection Manifold can be used, which can allow for representative gas sample collection after passing through the flow meters.

In some embodiments, the system can comprise an analytical instrument suite, which can comprise a bank of analytical instruments that can be tailored to the requirements for the investigation. In some embodiments, the analytical instrument suite can comprise: meters to measure % LEL, CO, O2 and H2S; a thermochemical sulfur detector; one or more gas chromatographs ("GC"); one or more gas chromatograph mass spectrometers ("GC-MS"); an off-axis integrated cavity output spectrograph ("OA-ICOS"); and a cavity ring down laser spectrograph ("CRDS").

Figure 2:
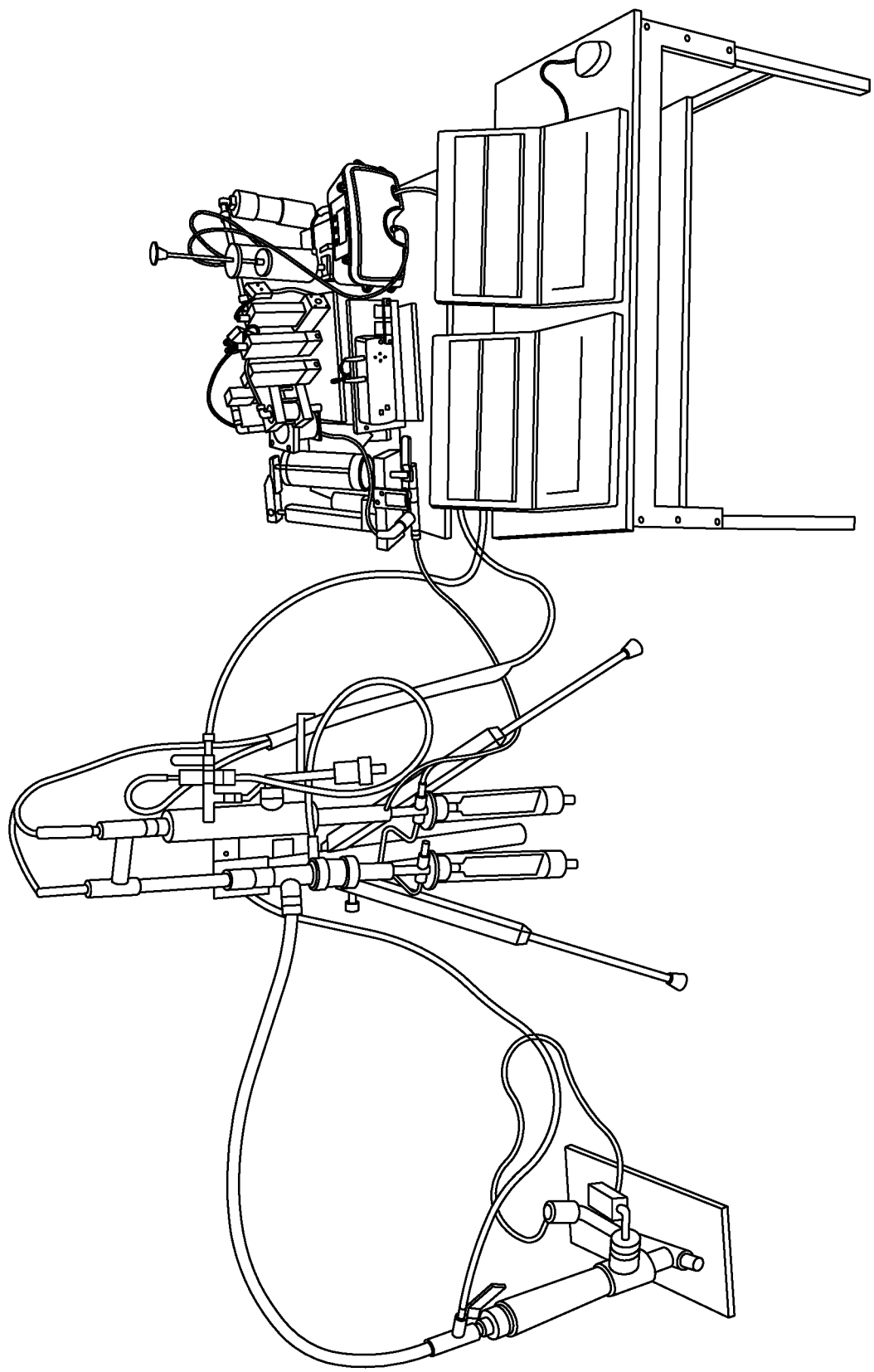
FIG. 2 is a photograph depicting a prototype of the system of FIG. 1.
Figure 3:
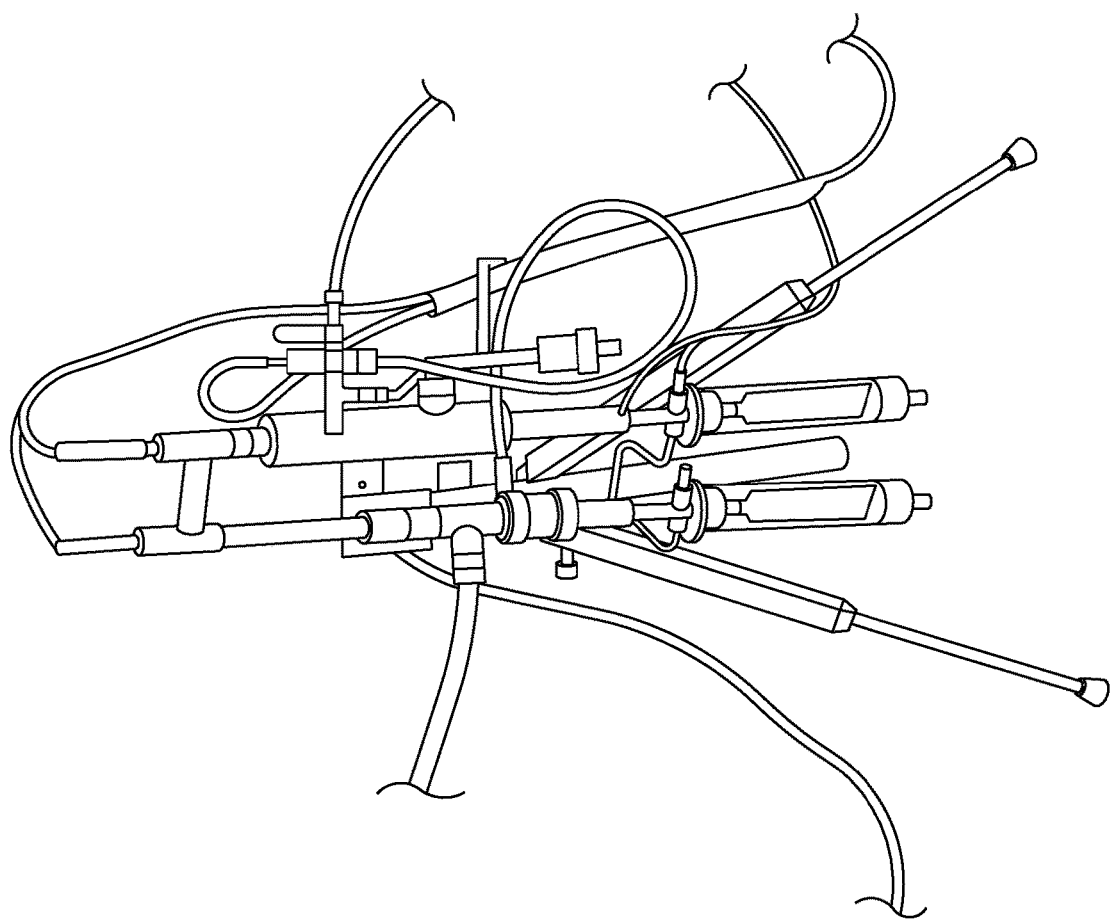
FIG. 3 is a photograph depicting a gas manifold of the prototype system of FIG. 2.
Figure 4:
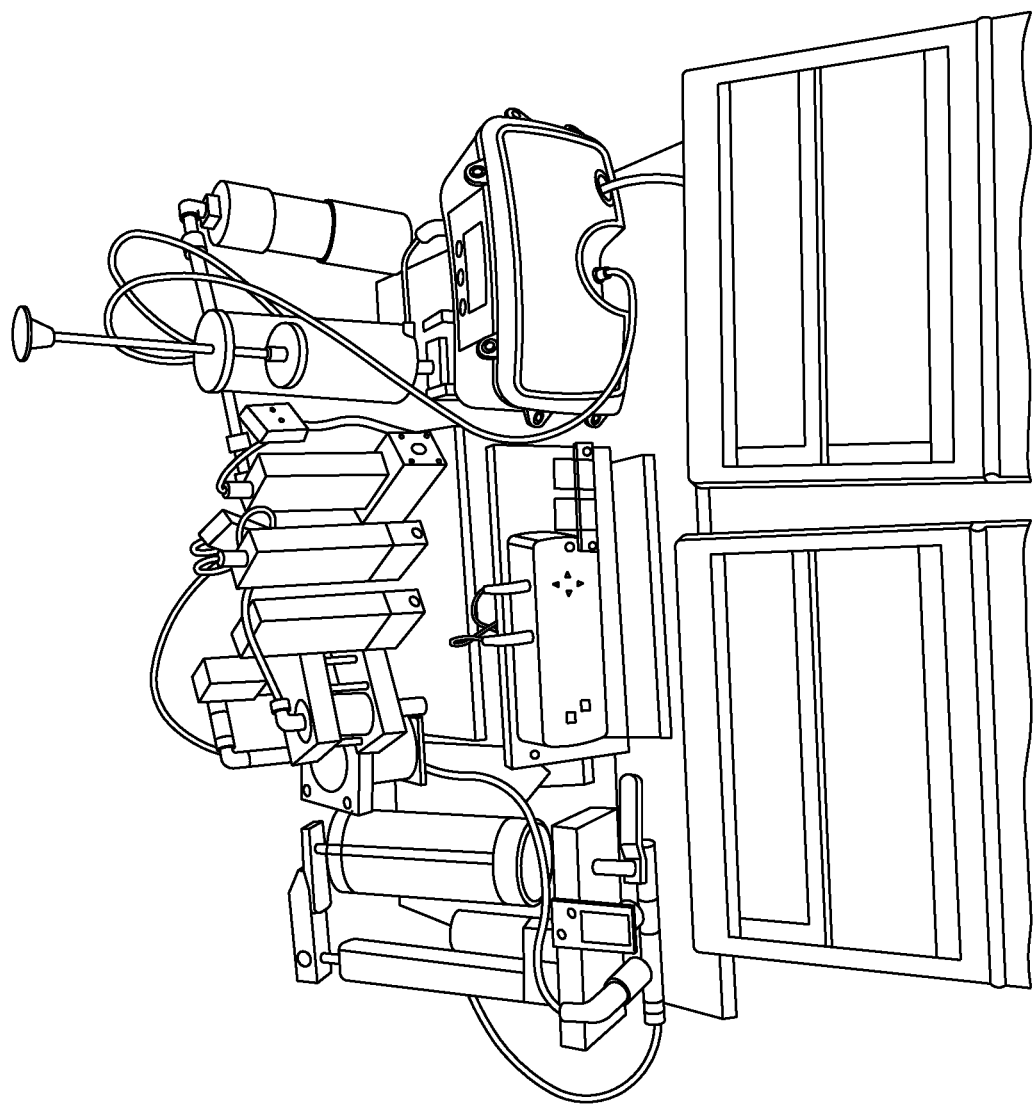
FIG. 4 is a photograph depicting flow meters of the prototype system of FIG. 2.

Referring to FIGS. 2, 3 and 4, photographs of a prototype of the system described herein is shown.

Figure 5:
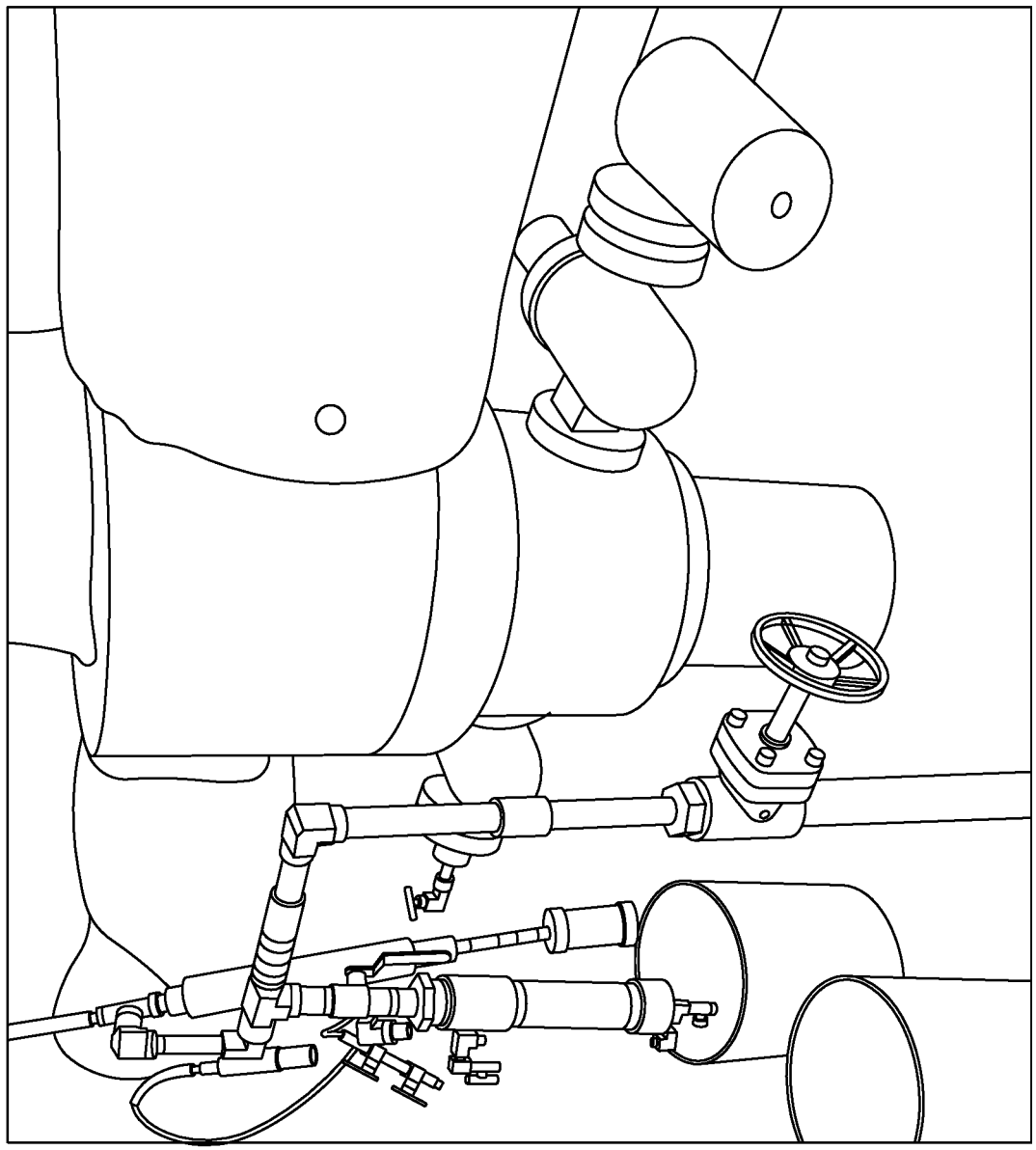
FIG. 5 is a photograph depicting a primary heat exchanger of the system of FIG. 1 connected to a well casing vapour flux chamber of a first well.
Figure 6:
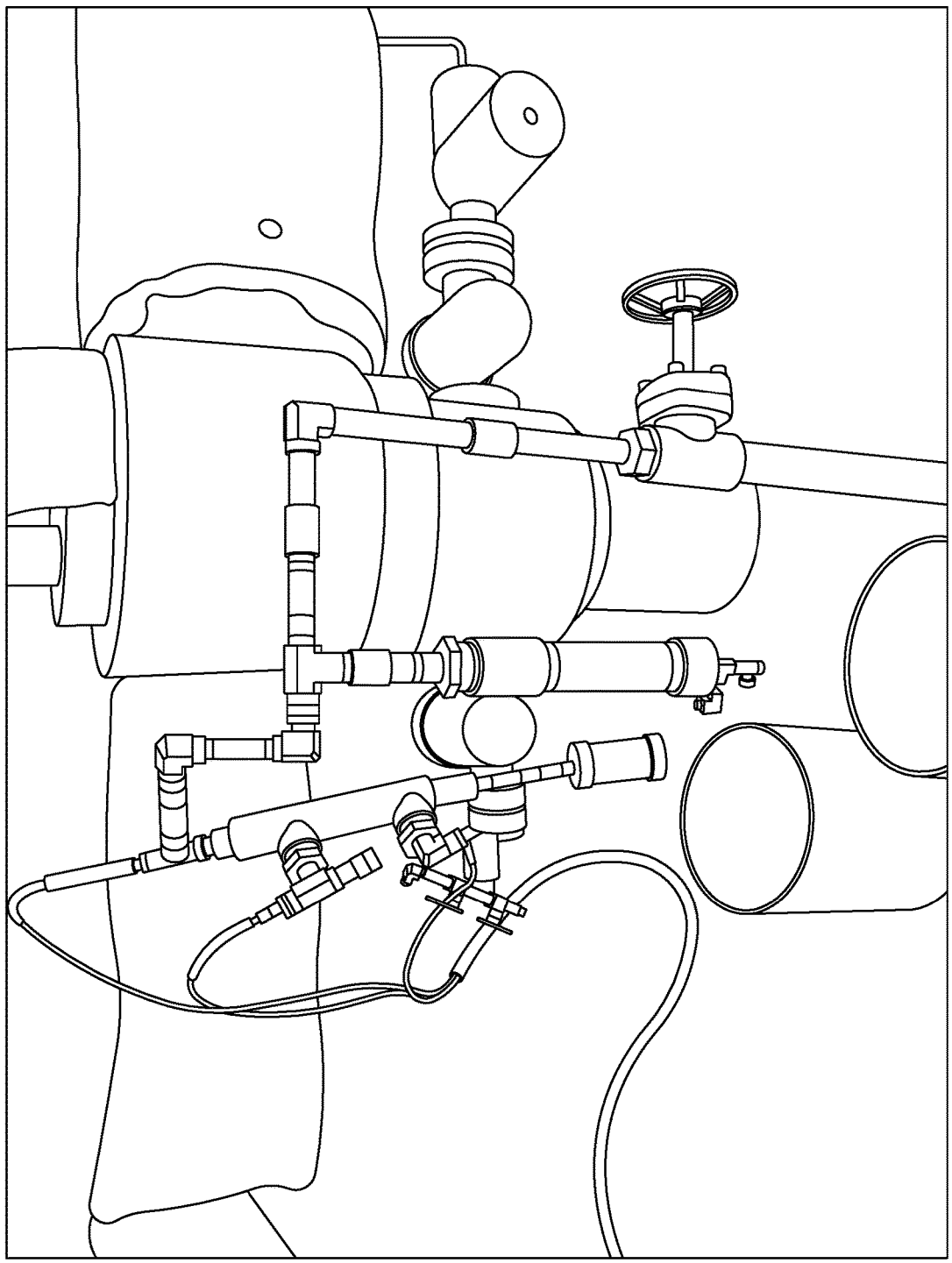
FIG. 6 is a photograph depicting a secondary heat exchanger connected to the primary heat exchanger of FIG. 5.

Referring to FIGS. 5 and 6, photographs of the primary and secondary heat exchangers of the system described herein is shown on a first well.

Figure 7:
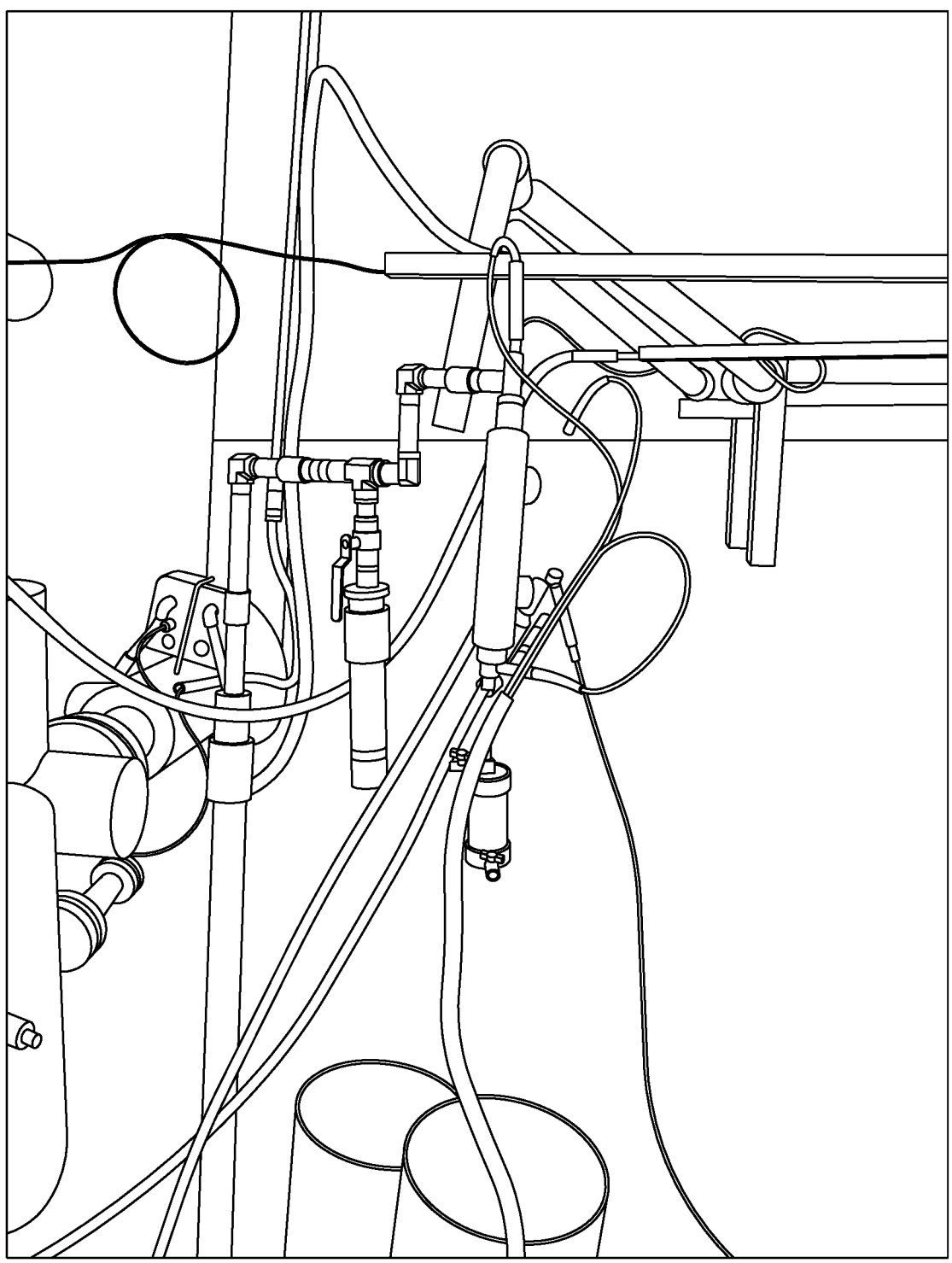
FIG. 7 is a photograph depicting the primary and secondary heat exchangers of the system of FIG. 1 connected to a well casing vapour flux chamber of a second well.

Referring to FIG. 7, a photograph of the primary and secondary heat exchangers of the system described herein is shown on a second well.

Figure 8:
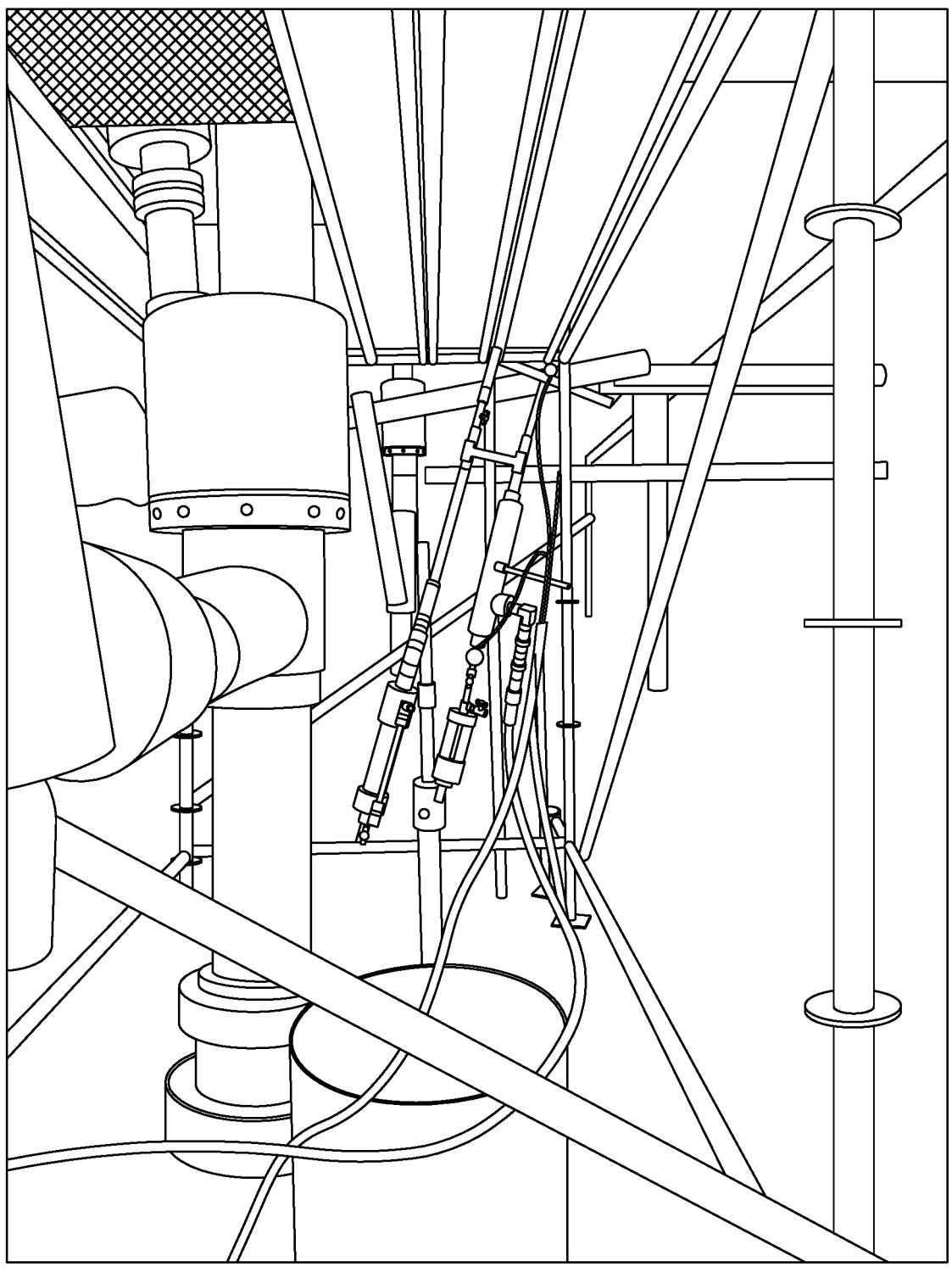
FIG. 8 is a photograph depicting the primary and secondary heat exchangers of the system of FIG. 1 connected to a well casing vapour flux chamber of a third well.

Referring to FIG. 8, a photograph of the primary and secondary heat exchangers of the system described herein is shown on a third well.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

I claim:

1. A gas and fluid measurement system configured for collecting natural gas and fluids samples from a well casing vapour flux chamber that are isolated from the atmosphere, the system comprising:
   a) a primary heat exchanger configured for operatively coupling to the well casing vapour flux chamber and receiving a sample of natural gas and fluids therefrom, the primary heat exchanger configured for removing water from the sample thereby producing a first processed sample;
   b) a primary pressure water bladder collection bag operatively coupled to the primary heat exchanger, the primary pressure water bladder collection bag configured to receive the water removed by the primary heat exchanger;
   c) a secondary heat exchanger configured for operatively coupling to the primary heat exchanger and receiving the first processed sample, the secondary heat exchanger configured for removing further water from the sample thereby producing a second processed sample;
   d) a secondary pressure water bladder collection bag operatively coupled to the secondary heat exchanger, the secondary pressure water bladder collection bag configured to receive the water removed by the secondary heat exchanger; and
   e) a gas drier/conditioner configured for operatively coupling to the secondary heat exchanger and receiving the second processed sample, the gas drier/conditioner further configured to produce a primary gas sample.

2. The system as set forth in claim 1, further comprising a gas collection manifold operatively coupled to the gas drier/conditioner, the manifold configured to isolate and collect gases without disrupting continuous monitoring, the manifold further configured to contain the gases with minimal isotope fractionation.

3. The system as set forth in claim 1, further comprising at least one flow meter and a pressure displacement meter.

4. The system as set forth in claim 3, further comprising at least one data-logger operatively coupled to the at least one flow meter and the pressure displacement meter, the at least one data-logger configured to measure, monitor and data-log gas flows, temperatures and pressures.

5. The system as set forth in claim 1, further comprising at least one analytical instrument configured for real-time in-situ monitoring, detection and measurement of the second processed sample.

6. The system as set forth in claim 5, wherein the at least one analytical instrument comprises one or more of a group comprising of gas chromatographs, gas chromatograph spectrometers, trace gas analyzers, off-axis integrated cavity output spectrographs, cavity rind-down laser spectrographs, Fourier transform infrared spectrographs, ion chromatographs, liquid chromatographs, liquid chromatograph mass spectrometers and solid phase extraction devices.

\* \* \* \* \*